United States Patent
Arnold

(10) Patent No.: US 7,834,624 B2
(45) Date of Patent: Nov. 16, 2010

(54) METHOD AND DEVICE FOR DETECTION OF THE POSITION OF AN EXAMINATION PERSON IN A MAGNETIC RESONANCE SYSTEM

(75) Inventor: Thomas Arnold, Nürnberg (DE)

(73) Assignee: Siemens Aktiengesellschaft, Munich (DE)

( * ) Notice: Subject to any disclaimer, the term of this patent is extended or adjusted under 35 U.S.C. 154(b) by 237 days.

(21) Appl. No.: 12/044,139

(22) Filed: Mar. 7, 2008

(65) Prior Publication Data

US 2008/0218166 A1 Sep. 11, 2008

(30) Foreign Application Priority Data

Mar. 9, 2007 (DE) .................... 10 2007 011 695

(51) Int. Cl.
G01V 3/00 (2006.01)
A61B 5/05 (2006.01)

(52) U.S. Cl. ............... 324/307; 324/309; 324/318; 324/314; 600/410; 600/411; 600/415

(58) Field of Classification Search ......... 324/300–322; 600/407–435; 353/122; 378/4, 8, 20
See application file for complete search history.

(56) References Cited

U.S. PATENT DOCUMENTS

| 3,528,000 | A | * | 9/1970 | Schwede ............... 324/303 |
| 5,551,430 | A | * | 9/1996 | Blakeley et al. ........... 600/410 |
| 6,195,409 | B1 | | 2/2001 | Chang et al. ............... 378/20 |
| 6,629,762 | B2 | | 10/2003 | Okamoto et al. ........... 353/122 |
| 6,762,605 | B2 | | 7/2004 | Brinker et al. ............. 324/309 |
| 7,180,294 | B2 | * | 2/2007 | Kohlmuller ............... 324/318 |
| 2004/0081341 | A1 | | 4/2004 | Cherek et al. ............. 382/128 |
| 2006/0264737 | A1 | | 11/2006 | Faber et al. ............... 600/410 |
| 2007/0265813 | A1 | * | 11/2007 | Unal et al. ................. 703/2 |
| 2008/0132779 | A1 | * | 6/2008 | Heumann et al. .......... 600/415 |
| 2008/0218166 | A1 | * | 9/2008 | Arnold ..................... 324/307 |

OTHER PUBLICATIONS

Siemens AG Publication "Deformierbare Ganzkoerper-3D-Fusion von MR-CTM Bildern zur Vollautomatischen Schichtplanung," Carstens (2007).

* cited by examiner

Primary Examiner—Brij B. Shrivastav
Assistant Examiner—Tiffany A Fetzner
(74) Attorney, Agent, or Firm—Schiff Hardin LLP

(57) ABSTRACT

In a method and arrangement for detection of the position of an examination person on a table in a magnetic resonance system, the examination person on the table is moved relative to the magnetic resonance system, RF pulses are radiated while the examination person is moved through the magnetic resonance system, the resulting magnetic resonance signals caused by the RF pulses are detected and the position of the examination person is determined using the acquired magnetic resonance signals.

22 Claims, 3 Drawing Sheets

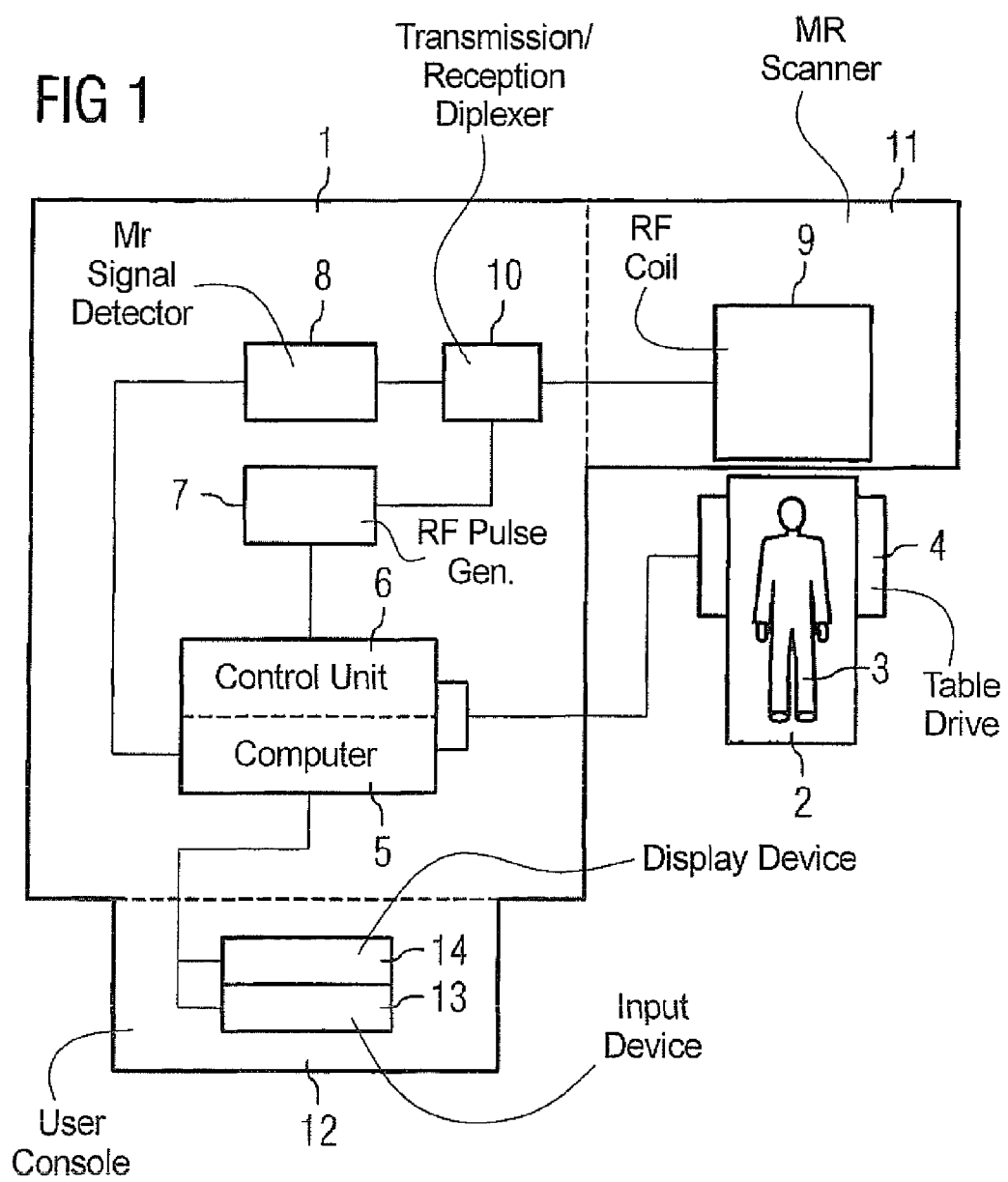

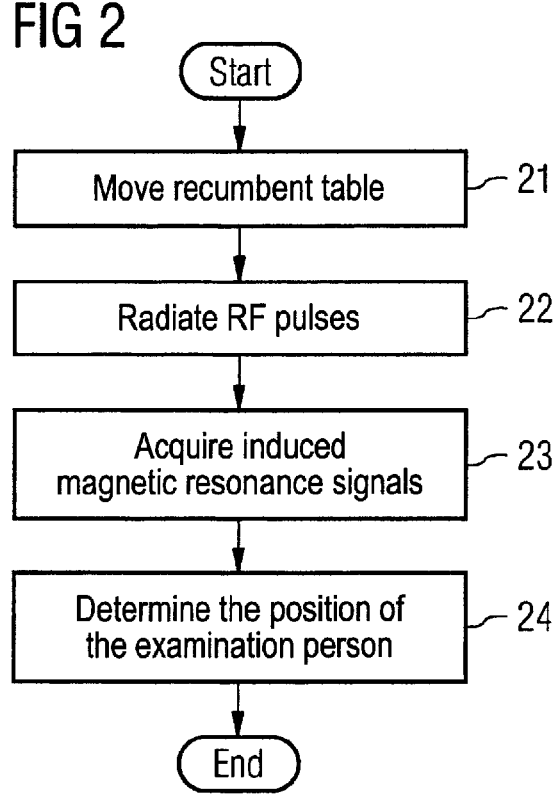
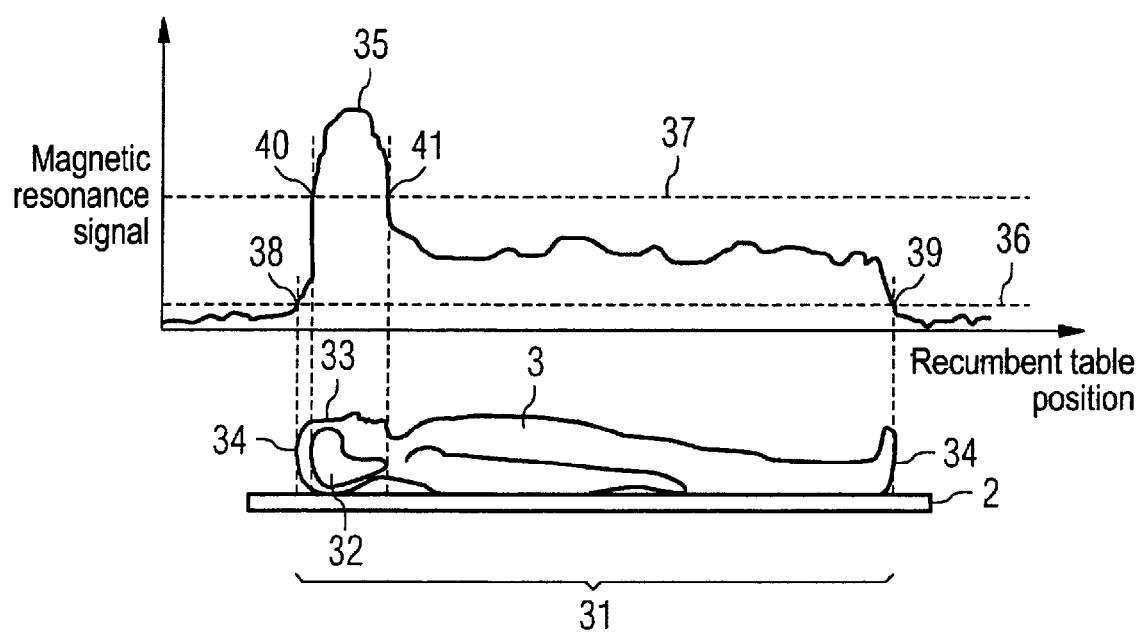

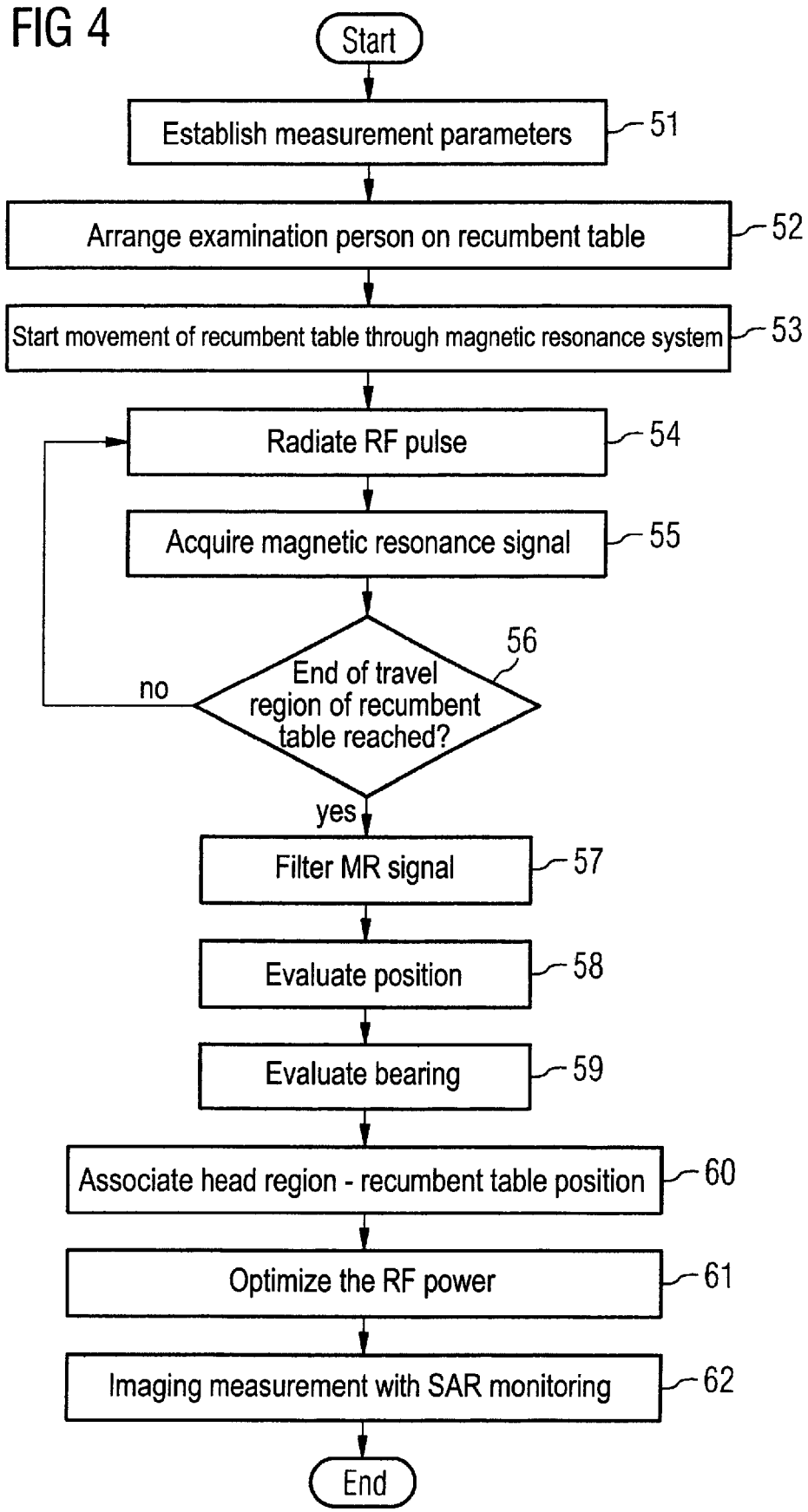

METHOD AND DEVICE FOR DETECTION OF THE POSITION OF AN EXAMINATION PERSON IN A MAGNETIC RESONANCE SYSTEM

BACKGROUND OF THE INVENTION

1. Field of the Invention

The present invention concerns a method and a device for detection of the position of an examination person in a magnetic resonance system, in particular for detection of the position and/or the orientation of an examination person on a horizontal table in a magnetic resonance system.

2. Description of the Prior Art

In an imaging magnetic resonance measurement or data acquisition (MR measurement) the quality of the images, the density of the slices in which imaging MR measurements are made and the speed with which the MR measurement can be executed increase with the radiated radio-frequency power (RF power). Only a certain maximum RF power can be used due to the absorption of the radio-frequency radiation (RF radiation) in the body tissue. The maximum allowable absorption is legally established with limit values for the specific absorption rate (SAR) that differ according to various sub-regions of the human body.

During an MR measurement the radiated RF power is continuously monitored in order to not exceed the legally dictated SAR limit values. Depending on the body regions exposed in the magnetic resonance system (MR system), the SAR monitoring determines the limit value for the allowed RF power and continuously monitors compliance therewith.

During an MR measurement, only the position of the table on which an examination person lies can be deduced. Additional information about the position of the examination person on the table (initial and end positions of the body) and about the orientation of the examination person (head-first or feet-first) is therefore required for the determination of the exposed body regions. Only with such information is it possible for the SAR monitoring to exactly determine which body regions will lie in which table position within the apparatus for a planned MR measurement.

The problem is further aggravated in the case of MR measurements in which the table is moved during the MR measurement (what are known as move during scan measurements, MDS measurements). During these MR measurements the exposed body regions must be continuously determined using the current table positions in order to determine and to monitor a possibly different limit value for the RF power.

The problem thus exists that information about the position and orientation of the examination person on the table is required for the determination of the exposed body regions and the monitoring of the SAR limit values.

Conventional MR systems are presently not designed to automatically establish the position and orientation of an examination person.

The present problem is addressed in part in MR systems according to the prior art by the operator being required to manually input the orientation of the examination person in the registration of the examination person. Although the body size of the person can likewise be input, this field is optional and, based on experience, is seldom filled out. However, the exact position of the body ends of the examination person on the table is not known even given input of the body size. In particular the precise knowledge of the head position of the patient is of importance because the lowest SAR limit value (which most severely limits the allowed RF power) exists for this body region.

In these conventional MR examinations missing information is determined through plausibility assumptions. For example, given an orientation with the head first it is assumed that the head lies at the position of the head coil when this coil is connected. The probable body size of the examination person is determined from statistical population data using the examination person's age, which is likewise to be filled out as an obligatory field in the registration. Assumptions about the position of the various body regions relative to the MR system are made by the SAR monitor on the basis of the probable body size. These assumptions can be very imprecise since the actual size of the examination person can deviate severely from the statistical mean. Moreover, these assumptions are no longer reliably possible given a feet first orientation. A worst-case estimation of the SAR limit value for the entire body is simply implemented. Due to the necessary safety tolerances, this estimation generally leads to too-low allowable RF powers that are too low, and thus significant limitations in the capability (number of slices, flip angle) of the appertaining MR measurements are made.

In other MR systems in the prior art, the aforementioned problem is also circumvented by simplified SAR models are used to determine the maximum allowable RF power. These models are largely independent of the position and orientation of the examination person. Due to the lack of discrimination of the exposed body regions, only a lower RF power can generally be used than would be possible according to legal SAR limit values for the respective body region. The capability of the MR measurements in these conventional MR systems is thereby limited relative to MR measurements with the maximum legally allowed RF power.

European Patent Application EP 1382300 A1 discloses a method and a device for positioning a patient in a medical diagnosis or therapy apparatus. In the described method, an image of the examination person is acquired with an image acquisition apparatus and the positions of various body regions are automatically determined by image processing. A scan region for a MR measurement is subsequently automatically suggested. The system is very complicated and requires both additional apparatuses (such as image acquisition apparatuses and computers) and programs for image processing with automatic detection of body regions.

The orientation of the examination person is typically manually input and the position of the examination person is estimated on the basis of assumptions. The manual input requires time on the part of the user and interrupts her or his workflow.

Moreover, due to the imprecise knowledge of the exposed body region, lower SAR limit values are used than the legally dictated SAR limit values. The RF power that is thereby reduced entails significant disadvantages for an imaging MR measurement such as, for example, longer measurement durations, a lower number of slices that are measured in a specific time, or a reduced image quality.

SUMMARY OF THE INVENTION

An object of the present invention is provide a method and a device that allow the position of an examination person on a table in a magnetic resonance system to be established automatically, simply and precisely. It should thereby be possible to integrate the method and the device into conventional magnetic resonance systems without greater expenditure.

The object is achieved in accordance with the present invention by a method for detection of the position of an examination person on a table in a magnetic resonance system that includes the steps of the table on which the examination person is arranged being initially moved relative to the magnetic resonance system, radio-frequency pulses (RF pulses) are radiated while the examination person is moved through the magnetic resonance system, the magnetic resonance signals that are induced by the RF pulses are subsequently acquired, the position of the examination person is subsequently determined using the acquired magnetic resonance signals.

The method offers the advantage that the position of the examination person on the table is immediately detectable from the magnetic resonance signal. The "position of the examination person" encompasses both the actual position of the examination person or the orientation of the examination person, or both. Since the magnetic resonance signal is measured as a function of the table position, the position of the examination person on the table (meaning the positions of the body ends) can be determined with high precision that signal. The orientation of the examination person can also be determined from the magnetic resonance signal. The method thus has the advantage that position and orientation of the examination person on the table can be determined automatically and precisely. A further advantage of the method is that the determination of the position of the examination person occurs without manual input of the user, so the workflow of the user is optimized. Moreover, the method can be integrated into a conventional magnetic resonance examination system without great effort.

In an embodiment of the present invention, a number of RF pulses are radiated upon movement of the table through the magnetic resonance system. A low number of RF pulses (for example between 1-4 pulses) are radiated at a table position, and the magnetic resonance signal induced by one to four RF pulses is read out during a readout gradient. The radiation of only a few RF pulses and the readout with only one readout gradient has the advantage that a magnetic resonance signal can be acquired in a very short time. The duration for the excitation with an RF pulse can thereby be only 50 ms and the duration for the readout only 150 ms. The movement of the table can thereby ensue step-by-step or continuously. When the movement ensues continuously, the region through which the table moves during the radiation and the readout is then defined as a table position. Since the table often moves slowly (for example with a speed of $\leq 50$ mm/s), this region is generally very small. This means that a smearing of the magnetic resonance signal due to the continuous table movement is generally insignificant. For this reason a table position upon radiation of the RF pulse can be meaningfully designated even given continuous table movement. It is not necessary to acquire so many magnetic resonance signals at one table position that a magnetic resonance image can be generated. A low number of RF pulses (for example less than 5) for every table position is sufficient in order to draw a conclusion about the position of the examination person from the detected magnetic resonance signal.

In a further embodiment of the invention the table is held stationary upon radiation of the RF pulse and readout of the magnetic resonance signal and a stationary MR measurement is effected at various table positions. The table is stationary during the radiation and the readout, which has the advantage that generally no smearing of the magnetic resonance signal occurs. However, the necessity can exist to measure and evaluate an entire slice block with the same coverage at every position. One reason for such a necessity can be the number of the required data points. A series of stationary MR measurements is effected at different positions of the table. The positions can thereby be predetermined or have a predetermined interval (separation; distance) from one another.

In a preferred embodiment of the invention, the induced magnetic resonance signal is optimized such that the magnetic resonance signal that originates from a predetermined body tissue of the examination person is higher than the magnetic resonance signal that originates from the rest of the body of the examination person. A dedicated magnetic resonance excitation is used in order to differentiate a predetermined body tissue from other body tissues. An inventive embodiment employs a magnetic resonance signal that is optimized such that the magnetic resonance signal that originates from the brain tissue of the examination person is higher than the magnetic resonance signal that originates from the rest of the body of the examination person. The brain tissue should be clearly discriminated from other body tissues (in particular the extremities). The goal of the dedicated excitation is not the acquisition of an anatomical 2D image for later pattern recognition, but rather the generation of an excitation in the brain tissue that, upon readout with a single readout gradient, generates a magnetic resonance signal that differs from the magnetic resonance signals from the remaining body tissue. Given a dedicated excitation, the magnetic resonance signal can be used to determine the orientation (thus the differentiation between head end and foot end) of the examination person. The table position of the brain tissue can be determined from the magnetic resonance signal (in particular when the excitation is optimized for brain tissue), from which the table position of the head of the examination person follows (and from which the orientation of the examination person can be determined). For example, $T_1$-weighted or $T_2$-weighted signals can be acquired for optimization of the magnetic resonance signal. Given a $T_1$ weighting, a pulse sequence of an inversion pulse and a detection pulse can be used that is optimized such that different signals are acquired from the predetermined body tissue and the remaining body tissue due to different $T_1$ relaxation times. The excitation can also be optimized for a $T_2$ weighting, wherein a differentiation of the body tissue due to different $T_2$ relaxation times is enabled. In general an excitation that is optimized in this manner should be used such that a magnetic resonance signal optimized for the differentiation of the body tissue is acquired.

In an inventive embodiment the magnetic resonance signal is associated with the body of the examination person when it lies above a first predetermined level value. In a further embodiment the magnetic resonance signal is associated with the rest of the body of the examination person when it lies above a first predetermined level value and below a second predetermined level value. The first level value advantageously lies above the noise level of the magnetic resonance signal that is measured when no body tissue that is excited by the RF pulses is located in the slice. The excitation of a slice with RF pulses and the acquisition of a magnetic resonance signal generally occur in the measurement region of the MR system. The first level value advantageously lies below the magnetic resonance signal that is measured when body tissue of the rest of the body is located in the measurement region. The second level value advantageously lies above the magnetic resonance signal that is measured when body tissue of the rest of the body is located in the measurement region but below the magnetic resonance signal that is measured when the predetermined body tissue is located in the measurement region. In general it can thus be assumed that body tissue is located in the measurement region for the table positions for which the magnetic resonance signal lies above the first level value. The position of the body ends of the examination person on the table can therefore be determined using the magnetic resonance signal. The manner of the excitation is thereby generally irrelevant since it depends only on a differentiation between noise level and actual magnetic resonance signal by means of a threshold (first level value).

According to a further embodiment the magnetic resonance signal lies above a second predetermined level value when it originates from the predetermined body tissue of the examination person. The magnetic resonance signal advantageously lies above the second level value when it originates from brain tissue of the examination person. The position of the predetermined body tissue can thus be established using the second level value. The head position of the examination person thus results for brain tissue, which has the advantage that the orientation of the examination person can be determined.

In the determination of the position of the examination person a transverse slice of the examination person is advantageously excited with the RF pulse and the magnetic resonance signal from this slice is read out during a readout gradient. The magnetic resonance signal can be filtered (for example to eliminate artifacts) before the evaluation.

During the determination of the position of the examination person the table can be moved through its maximum travel distance, or it can also be moved through a predetermined length that is at least as long as the head of the examination person. This has the advantage that the table does not have to be moved over the maximum travel length and that in spite of this the orientation of the examination person can generally be established. The fact that the head of the examination person is located at the front of the table in the movement direction can be established by, when the table is moved over a predetermined length in the forwards direction, the magnetic resonance signal exceeding the second level value within this region and subsequently falling to a value between the first level value and the second level value and remaining there. When the magnetic resonance signal only exceeds the first level value within this movement region and remains below the second level value, it can be assumed that the examination person is lying with feet first on the table.

In a preferred embodiment of the invention, the body region that is exposed to the RF pulses at a specific position of the table is determined from the specific position of the examination person. The power of the RF pulses for an imaging MR measurement can now be established such that predetermined absorption rates for the body region that is irradiated with RF pulses at a specific position of the table are not exceeded. The predetermined absorption rates can be, for example, SAR limit values for the respective body region. This procedure has the advantage that the maximum allowable RF power for the respective body region can be used due to the knowledge of the irradiated body region, which, as a consequence, achieves better efficiency in the imaging MR measurement. The knowledge of the body region irradiated at a specific table position can also be utilized for the monitoring of the compliance with the limit values for radiation absorption of the respective body region. This monitoring, known as SAR monitoring, can ensue both for a continuous movement of the table during the MR measurement (MDS measurements) and for stationary MR measurements. Moreover, the knowledge of the position of the examination person on the table can be used for a planning an imaging measurement. For example, the table region can be established for which an imaging measurement should ensue. The region can encompass the entire body of the examination person, i.e. from head end to foot end, and the measurement is accelerated since no regions are measured outside of the body of the examination person. Alternatively, the region may encompass only a predetermined body region of the examination person. An imaging measurement thus can be automatically implemented for a predetermined body region based on the knowledge of the table positions of the body regions.

The magnetic resonance signal for detection of the position of the examination person is advantageously measured during an adjustment measurement in which the table is moved continuously or step-by-step. This embodiment has the advantage that no additional MR measurement is required to determine the position, so a time and cost savings are achieved. Such adjustment measurements typically are implemented at the beginning of an examination. For example, the adjustment measurement serves for the determination of the resonance frequency of the system, the determination of the necessary power for a 180° spin flip, the checking of the hardware for monitoring or the implementation of a brightness normalization, or the like. The inventive method can also be simultaneously implemented during these adjustment measurements, such that a manual input of the position can be foregone.

Alternatively, the magnetic resonance signal can be determined during an MR measurement that is implemented only for the purpose of the detection of the position of the examination person.

The present invention also encompasses a magnetic resonance system having a table with a drive that is designed such that the examination person arranged on the table can be moved relative to the magnetic resonance system, a device for detection of the position of an examination person on the table of the magnetic resonance system, an RF pulse generator for generation of RF pulses, a detector unit for acquisition of magnetic resonance signals induced by the RF pulses, and a computer that determines the position of the examination person using the acquired magnetic resonance signals. The magnetic resonance system is designed such that the position of the examination person on the table can be detected according to the inventive method described above. The drive can move the table step-by-step or continuously. A combined control and computer unit can be provided that optimizes the RF pulses for a dedicated excitation, i.e. for an excitation in which a predetermined body tissue is excited such that the magnetic resonance signal from the predetermined body tissue is higher than the magnetic resonance signal from the rest of the body of the examination person. The control and computer unit can also optimize the temporal sequence of the radiation of the RF pulses and the acquisition of the magnetic resonance signal. For example, two or more RF pulses can be radiated before the acquisition of a magnetic resonance signal. Moreover, the computer can receive data from all components of the magnetic resonance system and further process the data. For example, data about the position of the table can be obtained from the drive and can be evaluated together with the acquired magnetic resonance signal and static population data, for example with regard to the position of the examination person on the table or with regard to the table positions of body regions of the examination person. The position of the examination person on the table thus can be determined automatically and precisely.

BRIEF DESCRIPTION OF THE DRAWINGS

FIG. 1 schematically illustrates an embodiment of an inventive magnetic resonance system with which the position of an examination person on a table in the magnetic resonance system can be automatically determined.

FIG. 2 is a flowchart of an embodiment for detection of a position of an examination person on a table in accordance with the invention.

FIG. 3 schematically shows an examination person on the table with the magnetic resonance signal for different table positions.

FIG. 4 is a more detailed flowchart showing how the position of the examination person on the table is determined and how this information is used for optimization of the RF power in accordance with the invention.

DESCRIPTION OF THE PREFERRED EMBODIMENTS

FIG. 1 schematically depicts a magnetic resonance system 1 with a patient table 2. The examination person 3 is arranged on the table 2. A drive 4 moves the table 2 relative to the magnetic resonance system 1. The magnetic resonance system has a computer 5 and a control unit 6 that communicate with one another. The control unit 6 monitors the position of the table 3 and communicates the table position to the computer 5. The magnetic resonance system 1 also has an RF pulse generator 7, a magnetic resonance signal detector 8, an RF coil 9 and a transmission-reception diplexer 10. The actual magnetic resonance measurement occurs in a scanner 11. In addition to the RF coil 9, the magnet 11 has the components furthermore necessary for MR measurements such as a basic field magnet and gradient coils (not shown for clarity). The table 2 with examination person 3 is inserted into the scanner 11 by the operation of the drive 4, to cause a body region of the examination person 3 to be located within the RF coil 9 dependent on the table position. A transverse slice of the examination person 3 is excited by an RF pulse emitted by the RF coil 9. The generation of the RF pulse occurs in the RF pulse generator 7 that is electrically connected with the RF coil 9 via the transmission-reception diplexer 10 and that is controlled by the control unit 6. The excitation generally occurs in the measurement region of the scanner 11 where the basic magnetic field exhibits the best homogeneity. The decay of the excitation causes a magnetic resonance signal that is detected (induced) in the RF coil 9 and that is acquired with the magnetic resonance signal detector 8. The RF coil 9 and the magnetic resonance signal detector 8 are electrically connected with one another via the transmission-reception diplexer 10. The acquired magnetic resonance signal is relayed to the computer 5.

Alternatively, a transverse slice of the examination person can be repeatedly excited by irradiation with successive RF pulses and a magnetic resonance signal is repeatedly acquired while the table 2 with the examination person 3 is moved continuously through the scanner 11. This radiation—acquisition cycle can last 200 ms and, given a table speed of 50 mm/s, can be executed once given a movement of one centimeter. The table 2 can alternatively be moved step-by-step, so the radiation and acquisition occur at predetermined positions of the table 2 and the table 2 is thereby held stationary for each acquisition. It may be necessary that an entire block composed of multiple slices be measured and evaluated with the same coverage, per table position.

The excitation of a transverse slice of the examination person 3 can ensue in two ways:

A non-specific excitation can be effected. For this type of excitation, it is only necessary that, from the excited slice of the examination person, a magnetic resonance signal can be detected that is greater than the noise level that is measured when no body tissue is located in the measurement region in which the excitation occurs. For this type of excitation, the control unit 6 causes the RF pulse generator 7 to generate an RF pulse with standard parameters, and this RF pulse is emitted by the RF coil 9. The magnetic resonance signal acquired in the magnetic resonance signal detector 8 is relayed to the computer 5. There it is determined at which table positions body tissues were located in the measurement region, and thus the position of the body ends of the examination person on the table is determined.

Alternatively, a dedicated excitation can be effected. In this type of excitation, an RF pulse is optimized such that a predetermined body tissue causes a higher magnetic resonance signal than the remaining body tissue upon excitation by the RF pulse. Alternatively, the temporal sequence of a number of successively radiated RF pulses or the temporal sequence of the radiation of one or more RF pulses and the acquisition of a magnetic resonance signal can be additionally optimized. The control unit 6 causes the RF pulse generator 7 to generate one or more RF pulses that are optimized such that a dedicated excitation occurs. The magnetic resonance signal caused by the dedicated excitation is acquired in the magnetic resonance signal detector 8 and is evaluated by the computer 5. If the excitation is optimized for brain tissue, for example, the computer 5 can establish the position of the head of the examination person on the table. With this information the computer 6 can establish the orientation of the examination person. Moreover, the remaining body tissue produces a magnetic resonance signal that lies above the noise level. The computer 5 thus can establish the position of the examination person as in the case of a non-specific excitation. In a dedicated excitation the orientation and the position of the examination person 3 on the table 2 thus can be simultaneously established. The dedicated excitation can also be coordinated with other body tissue or to processes in the body (such as, for example, to a beating heart with blood flow).

The magnetic resonance signal that is acquired by the magnetic resonance signal detector 8 after an excitation can be individual measurement values or a combination of a number of measurement values or a linking of a number of measurement values or measurement values to which algebraic operations were applied. It is important that the magnetic resonance signal (when it originates from body tissue) is higher than the noise level and that, for a dedicated excitation, the magnetic resonance signal is higher when it originates from predetermined body tissue than the magnetic resonance signal that originates from the rest of the body tissue. For example, the magnetic resonance signal can be represented as a number of signal curves. Different signal curves can be acquired, for example, by optimization of the excitation for a $T_1$ weighting or $T_2$ weighting. Depending on the body tissue, a $T_1$ weighting or a $T_2$ weighting or a combination of $T_1$-weighted and $T_2$-weighted signal curves can advantageously be used in order to acquire an optimized magnetic resonance signal.

The magnetic resonance system further has a user console 12 that includes an input device 13 and a display device 14. For example, if a non-specific excitation is used for detection of the position of the examination position, the orientation of the examination person 3 can be manually entered via the input device 13. The display device 14 can be used in order to display information about the position of the examination person 3 on the table 2, as well as other information necessary for the operation of a MR system. For example, the magnetic resonance signal can thus be displayed as a function of the table position.

In a dedicated excitation, the computer 5 determines the orientation and the position of the examination person 3 on the table 2. In a non-specific excitation, the computer 5 determines only the position of the examination person 3 and uses a manual input for the orientation. The size of the examination person 3 can be calculated from the position of the examination person 3. The computer 5 calculates the positions of the different body regions of the examination person 3 on the table 2 from the position and orientation of the examination person 3. The calculation can ensue using statistical data about the structure of the body of an examination person 3 of the determined size. The calculation can also ensue using the data that have been acquired by an MR measurement with dedicated excitation.

Using the positions of the body regions on the table 2, the computer 5 calculates the RF power that is possible at maximum for a specific table position without exceeding legally established SAR limit values for the body region located at the respective table position. The information about the maximum RF power dependent on the table position is relayed to the control unit 6. In a subsequent imaging MR measurement, the control unit 6 can use this information in order to radiate RF pulses with maximum possible power without the SAR limit values being exceeded. A greater efficiency of the imaging MR measurement is thereby achieved.

Moreover, the knowledge about the positions of the body regions together with the knowledge of the table position in an imaging MR measurement in which the table is moved continuously (move during scan measurement) can be used in order to determine which body region is exposed to the RF pulses at a specific point in time. The SAR limit values for this body region can be compared in the computer 5 with the RF power radiated at this point in time. SAR monitoring is thereby enabled. This monitoring can occur in real time. If the limit values are exceeded, the computer 5 can cause the control unit 6 to decrease the RF power so that the limit values are no longer exceeded.

A flowchart of an exemplary embodiment of the inventive method is shown in FIG. 2. The table 2 is moved in a first step 21. The table 2 can be moved continuously or in steps. An examination person 3 who is arranged on the table 2 is thereby moved together with the table 2. The movement occurs relative to the MR system. In general the table 2 is moved into the magnet of the MR system or out from this magnet. The movement of the table 2 can be controlled by the control unit 6. The position of the table 2 is communicated to the computer 5.

RF pulses are radiated in a second step 22. The RF pulses are radiated by means of the RF coil 9. In general the body regions that are located within the RF coil 9 are thereby exposed to the RF pulses. The RF pulses cause an excitation in the body tissue of the examination person 3 on the table 2 ("excitation' meaning an excited nuclear state). The excitation can occur in a transverse slice of a few millimeters to a few centimeters of thickness in the center of the apparatus. The radiated RF pulses thus can be optimized such that a dedicated excitation occurs, i.e. an excitation that enables a differentiation of various body tissue. In a dedicated excitation the RF pulses are optimized for a predetermined body tissue.

In a following third step 23 the magnetic resonance signals caused by the RF pulses are acquired. One possibility for acquisition of a magnetic resonance signal is to measure one or more measurement values, to subsequently process those values and to store the resulting magnetic resonance signal and relay it to the computer 5. Alternatively, the magnetic resonance signal may correspond to only one measurement value or a combination of measurement values. In general the measurement values are obtained by measurement of the voltage induced in the RF coil 9 upon decay of the excitation. Alternatively, local coils for signal acquisition or other methods can also be used.

Step 22 and step 23 ensue sequentially and this step sequence can be repeated arbitrarily often. In general the step sequence is executed repeatedly during the movement of the table 2, but it can also be executed at predetermined positions of the resting table 2. The table 2 is thereby moved step-by-step between the table positions. A number of step series can be executed at each table position, with different readout gradients being used for each step series, for example. Given a continuous table movement, the acquisition of the magnetic resonance signal normally ensues with only one acquisition gradient. Given a dedicated excitation with optimized RF pulses, a maximum magnetic resonance signal is generated in predetermined tissue. A maximum magnetic resonance signal in the predetermined tissue can also be achieved by the optimization of the time duration between the radiation of RF pulses (thus the time duration between the repetition of step 22) or by a radiation of a number of RF pulses before the acquisition of the magnetic resonance signal (thus a repeated execution of step 22 before the execution of step 23). Both the RF pulses and the time durations thus can be optimized in order to acquire a maximum magnetic resonance signal from a predetermined body region.

The position of the examination person 3 is determined in a fourth step 24. The determination occurs using the acquired magnetic resonance signals. The determination of the position includes the determination of the position of the examination person 3 on the table 2 and the determination of the orientation of the examination person 3. Position or orientation of the examination person 3 or both thus can be determined depending on the application. How the position and orientation of the examination person 3 are determined using the magnetic resonance signal is subsequently explained in more detail in connection with FIG. 3. The determination of the position is possible with a non-specific excitation; both the position and the orientation can be determined with a dedicated excitation. The size of the examination person 3 can also be determined from the position of the examination person 3. For an examination person 3 with a determined size the arrangement of the body regions relative to the body can be determined with the aid of statistical data. The region positions of the body regions on the table 2 can thus be determined from the position and the orientation of the examination person 3. This knowledge of the region positions can subsequently be used in order to determine which body region is irradiated with RF pulses at which table position. This information can be used in subsequent imaging MR measurements in order to optimize the RF power for the respective body region, such that the SAR limit values are not exceeded and such that the maximum possible RF power is available. Moreover, the information from the SAR monitoring can be used to determine the maximum allowable RF power in a subsequent imaging MR measurement. In general, the table position can be called up in real time. The irradiated body region is thus also known in real time, which is a requirement for an optimal capability of the SAR monitoring.

The method steps 21-24 described here can be executed as a separate MR measurement, as a pre-scan. Since only the radiation of one RF pulse or a small number of RF pulses is necessary at a table position, this pre-scan can be implemented in a significantly shorter time period that an imaging MR measurement. Alternatively, the method steps 21-24 can also be integrated into an adjustment measurement that is routinely executed before an imaging MR measurement. For example, given such an adjustment measurement the resonance frequency of the system is determined, the necessary power for a 180° excitation angle is determined, the hardware for the monitoring is checked and a brightness normalization is implemented. The integration of the method steps in such an adjustment measurement has the advantage that no additional MR measurement is necessary for detection of the position of the examination person. In both cases the detection of the position can ensue automatically without the necessity of a user input. The orientation of the examination person 3 can alternatively be manually input, so only the position of the examination person is automatically determined. No dedicated excitation is necessary in this case.

FIG. 3 shows a schematic depiction of an examination person 3 on the table 2 and an exemplary magnetic resonance signal 35 for various table positions. The curve course of the magnetic resonance signal is obtained via acquisition of a magnetic resonance signal at various table positions. The table 2 can be moved continuously or in steps. The magnetic resonance signal is induced via an excitation of a slice in the body of the examination person with one or more RF pulses. The curve course in FIG. 3 schematically shows the result of an exemplary MR measurement in which the table, 2 was moved continuously and a dedicated excitation of the brain tissue occurred. The magnetic resonance signal is shown dependent on the table position that was located in the measurement region at the point in time of the acquisition of the magnetic resonance signal. In order to identify which body region is located in the measurement region at this point in time, the examination person 3 is schematically depicted on the table 2. The table positions along the table 2 correspond to the table positions located above them on the horizontal axis of the chart.

The position 31 of the examination person on the table 2 can be described with the table positions of the body ends 34 and 34 of the examination person. The orientation of the examination person 3 results from the table position of the brain tissue 32 in the head 33 of the examination person 3. It is assumed that the examination person 3 on the table 2 is moved head first through the measurement region. Initially no body tissue is located in the measurement region, to only a magnetic resonance signal corresponding to the noise level is acquired. Given further movement of the table 2 the skullcap of the examination person initially enters into the measurement region, so the magnetic resonance signal rises. Shortly thereafter the brain tissue 32 enters into the measurement region, so a maximum magnetic resonance signal is acquired. Given further movement of the table 2 the magnetic resonance signal drops again when the brain tissue exits from the measurement region and a medium magnetic resonance signal is acquired from the rest of the body of the examination person 3. The magnetic resonance signal again falls to the noise level after the foot end of the examination person has exited the measurement region.

The evaluation of the curve course of the magnetic resonance signal can ensue automatically. A first level value 36 is initially established that lies above the noise level but below the magnetic resonance signal of the rest of the body of the examination person. The first level value 36, for example, can be established based on experimental values, but it can also be established individually for each MR measurement by evaluation of the noise level or via similar methods. The table positions of the body ends 34 and 34 can be determined from the intersection points of the magnetic resonance signal 35 with the first limit value 36. This determination is very precise since the magnetic resonance signal rises and falls steeply upon entrance and exit of the body of the examination person 3 into and from the measurement region. The intersection points 38 and 39 are thereby clearly defined, thus the table positions of the body ends 34 and 34 are as well. It may occur, for example, that more than two intersection points 38 and 39 from the magnetic resonance signal 35 exist with the first level value 36 due to noise in the magnetic resonance signal. In this case the magnetic resonance signal can be filtered, for example by smoothing of the curve course with a low-pass filter. In general the separation of the magnetic resonance signal that originates from the body tissue from the noise level is large enough and the first level value is selected such that there are only two intersection points 38 and 39.

In a dedicated excitation of the brain tissue, a second level value 37 that lies above the first level value 36 is established such that the magnetic resonance signal lies above the second level value 37 when the magnetic resonance signal originates from the brain tissue 32, and such that the magnetic resonance signal lies below the second level value 37 when it originates from the remaining body tissue. The level value can be established, for example, based on experimental value, but it can also be individually established for each MR measurement by evaluation of the magnetic resonance signal or via similar methods. The magnetic resonance signal can be evaluated, for example, by averaging magnetic resonance signal values around the maximum value of the magnetic resonance signal and averaging magnetic resonance signal values from the middle region of the table 2, with the second limit value 37 being established between these average values. The dedicated excitation is advantageously optimized such that the magnetic resonance signal that originates from the brain tissue clearly differs from the magnetic resonance signal that originates from the remaining body tissue. Two intersection points 40 and 41 then result between the magnetic resonance signal 35 and the second level value 37, from which the table position of the brain tissue is apparent. The head position of the examination person 3 (and therewith his orientation) can be determined from the table position of the brain tissue. The excitation can also be optimized with respect to another predetermined body tissue or with respect to processes in the body of the examination person, from which table position the orientation of the examination person can be concluded. For example, a magnetic resonance signal can be acquired from the strong blood flow in the heart of the examination person by evaluation of characteristic decay times of a dedicated excitation, this magnetic resonance signal being higher than the magnetic resonance signal from the rest of the body of the examination person. The magnetic resonance signal from the predetermined body region thereby does not have to always differ so distinctly (as is depicted in FIG. 3) from the magnetic resonance signal from the rest of the body. A number of intersections between the curve course of the magnetic resonance signal 35 and the second limit value 37 may also occur, but this is non-critical since the table position of the body tissue experiencing a dedicated excitation does not have to be known with greater precision in order to determine the orientation of the examination person 3. Moreover, the magnetic resonance signal can be filtered (for example with a low-pass filter) in order to smooth the curve course in order to obtain only two intersection points 40 and 41.

A reasonable evaluation for detection of the position of an examination person is also possible with magnetic resonance signals that were acquired given a step-by-step movement of the table 2. If no dedicated excitation occurs, as stated above the position of the examination person 3 can thus be evaluated with the aid of the first limit value and the intersection points 38 and 39. In each case the size of the examination person 3 can be calculated with knowledge of the table positions of the body ends 34.

Moreover, a similar evaluation can ensue when only a portion of the table 2 is moved through the measurement region. When the MR measurement is effected over a length that is at least as long as the head of the examination person, the orientation of the examination person 3 can then be established given a dedicated excitation of the brain tissue. If the examination person is inserted head first into the measurement region, at least one magnetic resonance signal that lies above the second level value is measured at a table position, and by contrast no magnetic resonance signal above the second limit value is measured when the examination person is moved feet first through the measurement region. Furthermore, for an orientation with the head first, it is characteristic that the magnetic resonance signal falls from a value above the second level value to a value between the first level value and the second level value when the examination person on the table 2 is moved through the limited travel path through the measurement region. Moreover, the table position of one body end 34 can always be determined using an intersection point of the first limit value 36 with the magnetic resonance signal 35.

FIG. 4 shows a flowchart that represents the steps according to an embodiment of the inventive method. In a first step 51 the start parameters are established. Start parameters are, for example, the type of the body tissue that experiences a dedicated excitation or the travel path of the table 2 or whether a filtering of the magnetic resonance signal should ensue, or the like. The examination person 3 is arranged on the table 2 in the next step 52. In the following step 53 the table with the examination person 3 is moved through the measurement region of the MR system 1. The movement ensues continuously, but it can also ensue in steps. In step 54 an RF pulse is radiated that excites a transverse slice in the measurement region of the MR system 1. The resulting magnetic resonance signal is acquired in step 55. In step 56 it is subsequently checked (for example by the computer 5) whether the end of the travel path of the table 2 is reached. If this is not the case, steps 54 through 56 are repeated. A number of steps 54 can also be executed in succession to radiate a number of RF pulses. The temporal sequence of the steps 54 and 55 can also be varied in order to achieve an optimal dedicated excitation. The table 2 moves continuously during the steps 54 through 56. Steps 53 through 56 thereby represent the pre-scan, thus the MR measurement that is necessary for detection of the position of the examination person. As already described, these steps can also be integrated into an adjustment scan. No adjustment scan is provided in the flowchart shown here, but an adjustment scan could be inserted between step 52 and step 53, for example. If it is established in step 56 that the end of the travel range of the table 2 has been reached, the steps 57 through 60 are executed that serve for the evaluation of the magnetic resonance signal for position determination of the examination person 3. In step 57 the magnetic resonance signal is filtered, for example for smoothing or to remove artifacts. The position of the examination person 3 on the table 2 is evaluated in step 58 with the aid of the first level value 36. The orientation of the examination person 3 is evaluated in step 59 as described above with the aid of the second level value 37. The table positions of the different body regions of the examination person 3 are subsequently calculated in step 60. For this the size of the examination person 3 is determined from the table positions of the body ends and the distribution of the body regions in the respective examination person 3 with the determined size is calculated using statistical data. Since the position of the examination person 3 on the table 2 is known, the table positions of the body regions can now be calculated. The calculation is advantageously implemented by the computer 5. In step 61 the optimal RF power for the respective table position can be calculated with the knowledge of the table positions of the body regions. In this context, "optimal" means that the RF power does not exceed the maximum allowable RF power set by the SAR limit values, but also is not significantly less than the maximum allowable RF power. SAR monitoring is implemented during the imaging MR measurement; the knowledge of the body region that is irradiated at a specific table position is used in order to check that the maximum allowable RF power for the respective body region is not exceeded.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for detecting a position of an examination person in a magnetic resonance scanner, comprising the steps of:
   placing an examination person on a moveable table and operating the table with computerized system to move the examination person on the table at least partially through the magnetic resonance scanner;
   irradiating the examination person on the table with at least one RF pulse while the examination person and the table are moving through the magnetic resonance scanner, and thereby causing magnetic resonance signals to be emitted from the examination person that are insufficient by themselves for image generation;
   optimizing said at least one RF pulse to give a magnetic resonance signal originating from predetermined body tissue, at a known location within the examination person, a differing signal characteristic that differs from magnetic resonance signals originating from a remainder of the examination person;
   detecting said magnetic resonance signals correlated in said computerized system with moving the table through the magnetic resonance scanner; and
   automatically electronically determining a position of the examination person in the magnetic resonance scanner using only the acquired magnetic resonance signal, which has said differing signal characteristic, from the predetermined body tissue correlated with moving the table through said magnetic resonance scanner.

2. A method as claimed in claim 1 wherein said table reaches at least one table position while moving through the magnetic resonance scanner, and comprising:
   radiating a number of RF pulses in a range between 1 and 4 pulses with said table in said at least one table position, and
   generating a readout gradient and reading out a magnetic resonance signal, as said at least one magnetic resonance signal, generated by said number of RF pulses during said readout gradient.

3. A method as claimed in claim 1 comprising also automatically electronically determining an orientation of the examination person on the table using the detected magnetic resonance signals.

4. A method as claimed in claim 1 comprising optimizing the magnetic resonance signal emitted from the examination person to cause the magnetic resonance signal originating from predetermined body tissue of the examination person to be greater than the magnetic resonance signal originating from a remainder of the body of the examination person.

5. A method as claimed in claim 4 comprising optimizing said magnetic resonance signal to cause the magnetic resonance signal originating from brain tissue, as said predetermined body tissue, to be greater than the magnetic resonance signal that originates from the remainder of the body of the examination person.

6. A method as claimed in claim 5 comprising:
automatically electronically determining that said magnetic resonance signal originates from the remainder of the body of the examination person when said magnetic resonance signal is above a first signal level value, and automatically electronically determining that the magnetic resonance signal originates from said brain tissue when said magnetic resonance signal is above a second signal level value that is higher than said first signal level value.

7. A method as claimed in claim 4 comprising automatically electronically determining that said magnetic resonance signal originates from the remainder of the body of the examination person when said magnetic resonance signal lies above a predetermined signal level value.

8. A method as claimed in claim 7 wherein said predetermined signal level value is a first predetermined signal level value, and comprising:
automatically determining that said magnetic resonance signal originates from the remainder of the body of the examination person when said magnetic resonance signal is above said first predetermined level value and below a second predetermined level value that is higher than said first predetermined level value.

9. A method as claimed in claim 8 comprising automatically electronically determining that said magnetic resonance signal originates from the predetermined body tissue when said magnetic resonance signal is above said second predetermined level value.

10. A method as claimed in claim 1 comprising continuously moving said table with the examination person thereon through said scanner during radiation of said at least one RF pulse and detection of said magnetic resonance signal.

11. A method as claimed in claim 1 comprising:
moving said table with said examination person thereon through a plurality of table positions in said magnetic resonance scanner and temporarily holding said table and the examination person thereon stationary at each of said table positions and,
at each of said table positions, radiating said at least one RF pulse and detecting said magnetic resonance signal.

12. A method as claimed in claim 1 comprising:
exciting a transverse slice of the examination person by irradiating said at least one RF pulse, and
generating a readout gradient and reading out the magnetic resonance signal from said transverse slice during said readout gradient.

13. A method as claimed in claim 1 comprising filtering said magnetic resonance signal to eliminate artifacts therein before determining the position of the examination person using the detected magnetic resonance signal.

14. A method as claimed in claim 1 wherein said table is movable through a maximum travel distance relative to said magnetic resonance scanner, and comprising:
moving said table with the examination person thereon through said maximum travel distance, during which said at least one RF pulse is radiated and said magnetic resonance signal is detected.

15. A method as claimed in claim 1 comprising moving said table with the examination person thereon relative to said magnetic resonance scanner only through a predetermined length that is at least as long as the head of the examination person.

16. A method as claimed in claim 1 wherein said table has a leading edge that moves first through said magnetic resonance scanner, and automatically electronically determining that the head of the examination person is located closer to said leading edge than the feet of the examination person by detecting, as said table with the examination person thereon moves through the magnetic resonance scanner, that the magnetic resonance signal exceeds a second signal level value and subsequently falls to a signal value between said second level value and a first level value that is lower than said second level value in a region of the examination person that is closer to said leading edge of said table, and thereafter said magnetic resonance signal remains between said second level value and said first level value.

17. A method as claimed in claim 16 comprising automatically electronically determining a size of the examination person by identifying a range of the examination person during which said magnetic resonance signal is above said first signal level value.

18. A method as claimed in claim 1 comprising, from the automatically determined position of the examination person, also automatically electronically determining a body region of the examination person that is exposed to said at least one RF pulse at a specific position of the table in the magnetic resonance scanner.

19. A method as claimed in claim 18 comprising:
subsequently acquiring diagnostic magnetic resonance data from the body region of the examination person with the table at said specific position and
monitoring power of RF pulses radiated during acquisition of said diagnostic magnetic resonance data and
limiting said power so as to not to exceed a predetermined absorption rate for said body region.

20. A method as claimed in claim 1 comprising:
acquiring diagnostic magnetic resonance data from the examination person suitable for generating a magnetic resonance image of the examination person, and
radiating said at least one RF pulse and
detecting said magnetic resonance signal and
determining the position of the examination person before acquiring said diagnostic magnetic resonance data.

21. A method as claimed in claim 20 comprising using said position of the examination person determined from the magnetic resonance signal to plan the acquisition of said diagnostic magnetic resonance data.

22. A magnetic resonance system comprising:
a magnetic resonance scanner;
a patient table configured to receive an examination person thereon;
a computerized system configured to operate said table in order to move said table with the examination person thereon at least partially through the magnetic resonance scanner;
an RF system that irradiates the examination person on the table with at least one RF pulse while the examination person and the table are moving through the magnetic resonance scanner, and thereby causing magnetic resonance signals to be emitted from the examination person that are insufficient, by themselves, for image generation, said RF system being configured to optimize said at least one RF pulse in order to give a magnetic resonance signal originating from predetermined body tissue, at a known location within the examination person, a differing signal characteristic that differs from magnetic resonance signals originating from a remainder of the examination person; a detector that detects said magnetic resonance signals correlated in said computerized system with moving the table through the magnetic resonance scanner; and said computerized system being configured to automatically determine a position of the examination person in the magnetic resonance scanner using only the acquired magnetic resonance signal, which has said differing signal characteristic, from the predetermined body tissue correlated with moving the table through said magnetic resonance scanner.

* * * * *